United States Patent
Hershberger et al.

(10) Patent No.: US 11,793,133 B2
(45) Date of Patent: Oct. 24, 2023

(54) PHYTOPHTHORA RESISTANT CATHARANTHUS ROSEUS PLANT

(71) Applicant: SYNGENTA PARTICIPATIONS AG, Basel (CH)

(72) Inventors: Amanda Hershberger, Gilroy, CA (US); Inka Gawenda, Enkhuizen (NL); Darryl Thomas, Gilroy, CA (US); Jane Trolinger, Gilroy, CA (US); Sergio De La Fuente Van Bentem, Enkhuizen (NL); Jaemin Lee, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/891,597

(22) Filed: Jun. 3, 2020

(65) Prior Publication Data
US 2021/0259180 A1     Aug. 26, 2021

Related U.S. Application Data

(63) Continuation of application No. 15/545,345, filed as application No. PCT/EP2016/051418 on Jan. 25, 2016, now abandoned.

(60) Provisional application No. 62/108,682, filed on Jan. 28, 2015.

(51) Int. Cl.
| | | |
|---|---|---|
| A01H 1/02 | (2006.01) |
| A01H 5/02 | (2018.01) |
| A01H 1/00 | (2006.01) |
| A01H 1/04 | (2006.01) |
| A01H 6/08 | (2018.01) |

(52) U.S. Cl.
CPC .............. *A01H 1/1245* (2021.01); *A01H 1/02* (2013.01); *A01H 1/04* (2013.01); *A01H 5/02* (2013.01); *A01H 6/084* (2018.05)

(58) Field of Classification Search
None
See application file for complete search history.

(56) References Cited

U.S. PATENT DOCUMENTS

| | | | |
|---|---|---|---|
| 5,491,285 A * | 2/1996 | Bowman | A01H 5/02 Plt./226 |
| 6,166,306 A | 12/2000 | Bowman | |
| 2007/0283454 A1 | 12/2007 | Kitajima | |

FOREIGN PATENT DOCUMENTS

| | | |
|---|---|---|
| JP | 9-508022 | 8/1997 |
| WO | 9519698 A1 | 7/1995 |

OTHER PUBLICATIONS

Yandoc et al. Plant Disease (2007).*
Swati Chaudhary et al: "Characterization and genetic linkage mapping of the horticulturally important mutation() in periwinkle", Scientia Horticulturae, Elsevier Science Publishers, vol. 129, No. 1, Feb. 28, 2011, pp. 142-153.
Allard Robert Wayne ED—Allard Robert Wayne: "Principles of plant breeding, Passage", Jan. 1, 1960, Princiles of Plant Breeding, Wiley, New York, pp. 67-72.
International Search Report dated Mar. 16, 2016 from International Application No. PCT/EP2016/051418.
Hu et al., Mefenoxam sensitivity and fitness analysis of *Phytophthora nicotianae* isolates from nurseries in Virginia, USA, Plant Pathology, 2008, 57, 728-736.

* cited by examiner

*Primary Examiner* — Medina A Ibrahim
(74) *Attorney, Agent, or Firm* — Dale Skalla

(57) ABSTRACT

The present invention relates to plants of the genus *Catharanthus* containing a genetic resistance to *Phytophthora*. In particular, the present invention relates to a *Catharanthus roseus* plant containing a genetic resistance to the F and S isolates of *P. nicotianae*.

6 Claims, 6 Drawing Sheets

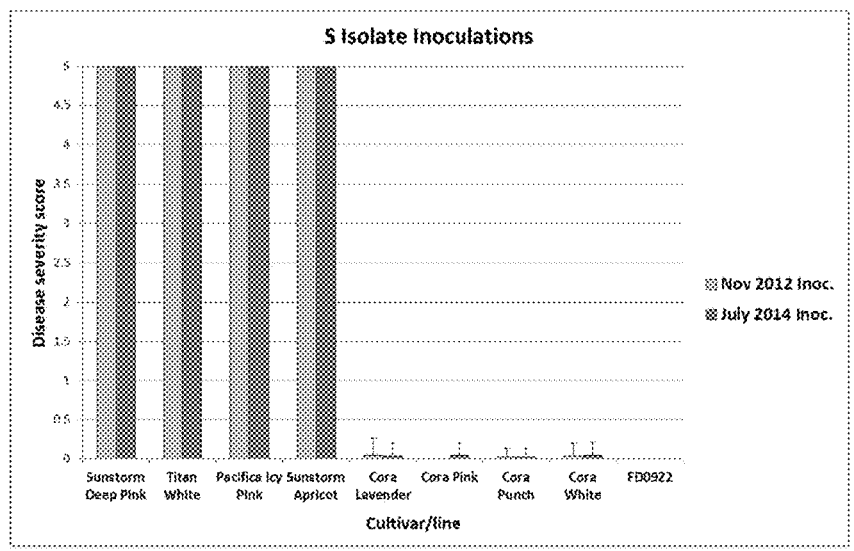
Figure 1. Disease severity scores of nine *Catharanthus roseus* cultivars/lines to S isolate inoculations over two dates.

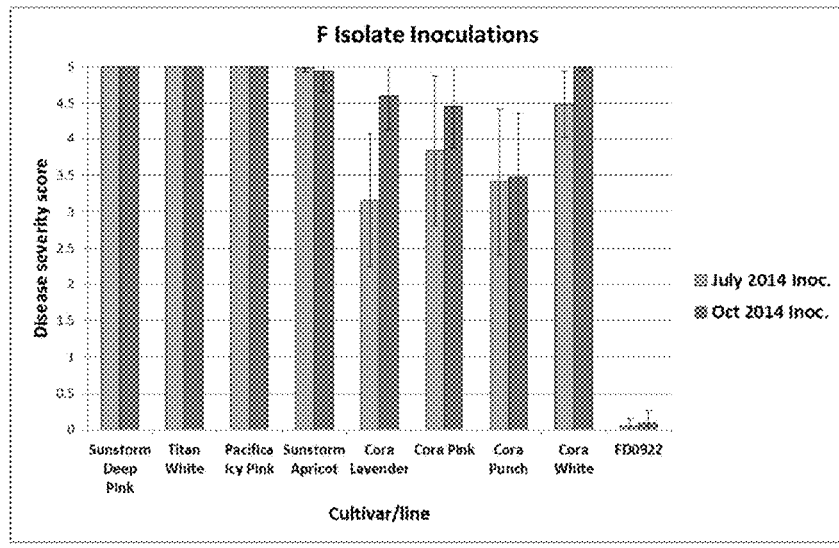
Figure 2. Disease severity scores of nine *Catharanthus roseus* cultivars/lines to F isolate inoculations over two dates.

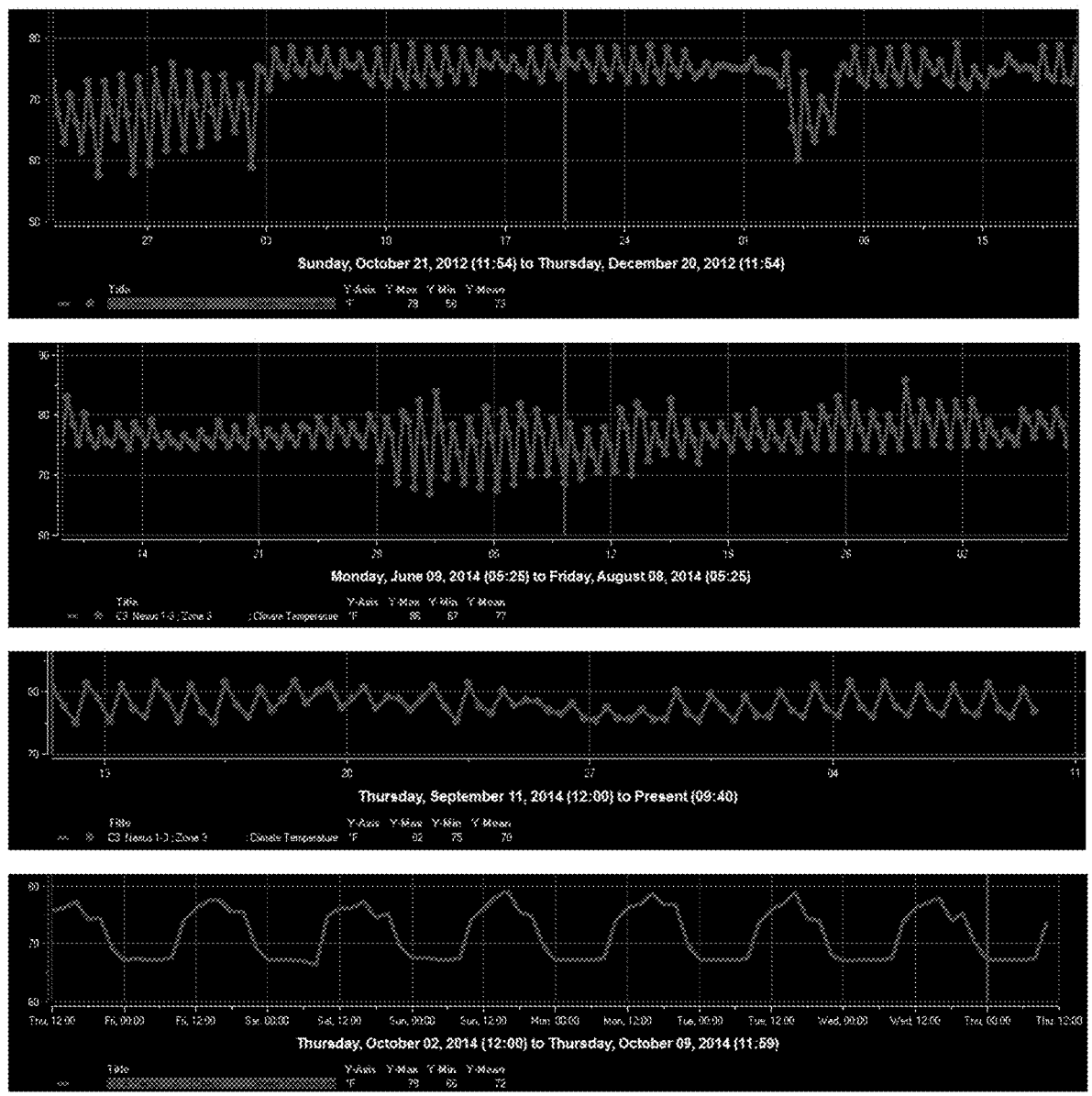
Figure 3. Temperature in greenhouses G3 and A1 on the dates shown a) G3: Nov 7 2012 – Dec 16 2012; b) G3: June 11 2014 – July 28 2014; c) G3: Sept 10-Oct 1 2014 G3; and d) A1 Oct 2 –Oct 30 2014

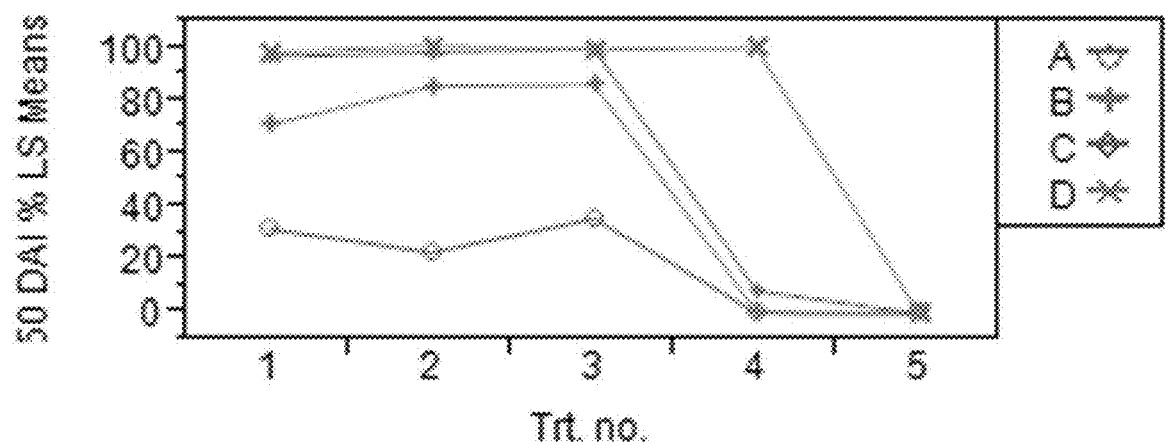
Figure 4. Interaction plot: Treatments*Cultivars

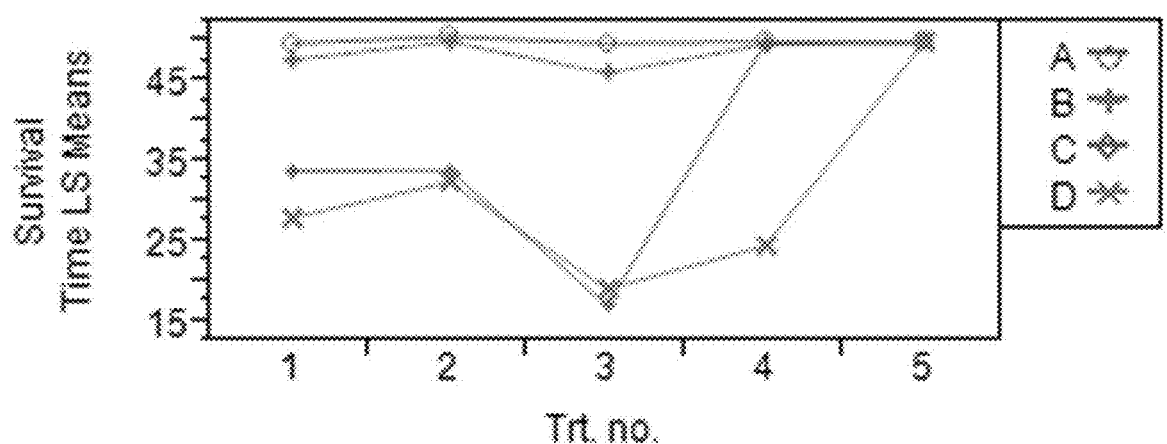
Figure 5. Interaction plot: Treatments*Cultivars

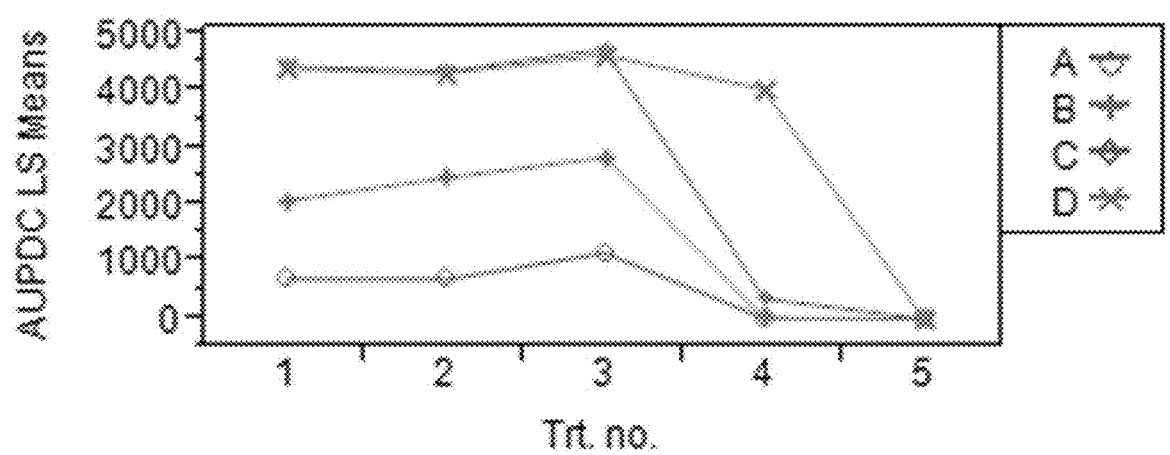
Figure 6. Interaction plot: Treatments*Cultivars

PHYTOPHTHORA RESISTANT CATHARANTHUS ROSEUS PLANT

RELATED APPLICATION INFORMATION

This application is a continuation of a U.S. application Ser. No. 15/545,345, filed Jul. 21, 2017, which is a 371 of International Application No. PCT/EP2016/051418, filed Jan. 25, 2016, which claims priority to U.S. provisional application No. 62/108,682, filed Jan. 28, 2015, the contents of which are incorporated herein by reference herein.

FIELD OF THE INVENTION

The present invention relates to Catharanthus roseus plants having a novel Phytophthora nicotianae resistant phenotype.

INTRODUCTION

Catharanthus roseus, known formerly as Vinca rosea is a main source of vinca alkaloids, now sometimes called Catharanthus alkaloids. There are about 130 of these compounds, including vincristine and vinblastine, common drugs used to treat cancer.

Catharanthus roseus is also cultivated as an ornamental plant in gardens. Several cultivars have been bred to produce flowers in many shades of pink, red, lilac, and white, or in light shades with dark eyes.

Catharanthus roseus (L.) G. Don (Madagascar periwinkle or annual C. roseus) has high levels of susceptibility to the plant pathogen Phytophthora nicotianae Breda de Haan (aerial Phytophthora). The presence of P. nicotianae routinely causes stem and foliage blight, and occasionally may cause root rot. P. nicotianae is one of the most economically important pathogens of C. roseus (Jeffers and Meadows, 2011). P. nicotianae is often called aerial Phytophthora because the disease normally occurs on the above-ground parts of C. roseus rather than causing a root rot as do many other Phytophthora diseases. Plants infected with that pathogen cannot be cured and normally die. Plantings of C. roseus often have 100% mortality if P. nicotianae is present. P. nicotianae can survive in infested soil for many years as chlamydospores resistant to environmental conditions.

P. nicotianae as a pathogen of C. roseus was first reported in India in 1916 (Dastur, 1916), and first reported in California in 1977 (Gill et al., 1977; Keim, 1977). C. roseus had become a popular bedding plant throughout the southern half of the United States, but by the late 1980's aerial Phytophthora on C. roseus was so widespread that C. roseus popularity declined substantially.

The present invention reveals for the first time a Catharanthus plant which is resistant to both the Florida and Syngenta isolates of P. nicotianae.

SUMMARY OF THE INVENTION

The present invention provides a Catharanthus plant containing a genetic resistance to Phytophthora, wherein a sample of representative seed of a plant containing a genetic resistance to Phytophthora is deposited under NCIMB Accession No. 42348.

The present invention provides a Catharanthus seed containing a genetic resistance to Phytophthora, wherein said seed is obtainable from a plant grown from seed deposited under NCIMB Accession No. 42348, or progeny thereof.

In one embodiment, said seed contains an allele for resistance the Syngenta (S) and Florida (F) isolates of P. nicotianae.

There is also provided a Catharanthus plant produced by growing the seed of the present invention.

There is also provided pollen of the plant of the present invention.

There is also provided an ovule of the plant of the present invention.

The present invention provides a method for producing $F_1$ hybrid Catharanthus seed comprising crossing a first parent Catharanthus plant with a second parent Catharanthus plant and harvesting the resultant $F_1$ hybrid *Catharanthus* seed, wherein said first or second parent *Catharanthus* plant is the *Catharanthus* plant of the invention.

There is also provided a hybrid seed produced by the method of the present invention.

There is also provided a hybrid plant or its parts produced by growing said hybrid seed of the present invention.

There is also provided seed containing said genetic factor to *Phytophthora* resistance produced from said hybrid plant of the present invention.

There is also provided viable *Catharanthus* seeds deposited under NCIMB Accession No. 42348 and plants grown from said deposited seeds and the progeny thereof, wherein the progeny contain the genetic factor to *Phytophthora* resistance.

DESCRIPTION OF THE FIGURES

FIG. 1 shows disease severity scores of nine *Catharanthus roseus* cultivars/lines to S isolate inoculations over two dates.

FIG. 2 shows disease severity scores of nine *Catharanthus roseus* cultivars/lines to F isolate inoculations over two dates.

FIG. 3 shows temperatures in greenhouses G3 and A1 on the dates shown.

FIG. 4 shows an interaction plot: Treatments*Cultivars

FIG. 5 shows an interaction plot: Treatments*Cultivars

FIG. 6 shows an interaction plot: Treatments*Cultivars

DETAILED DESCRIPTION OF THE INVENTION

The present invention provides a *Catharanthus* plant containing a genetic resistance to *Phytophthora*, wherein a sample of representative seed of a plant containing a genetic resistance to *Phytophthora* is deposited under NCIMB Accession No. 42348.

In one embodiment, the *Catharanthus* plant of the present invention is *Catharanthus roseus*. Alternatively, the *Catharanthus* plant may belong to another species including, but not limited to *Catharanthus coriaceus, Catharanthus lanceus, Catharanthus longifolius, Catharanthus* ovalis, *Catharanthus pusillus, Catharanthus scitulus*, and *Catharanthus trichophyllus*.

In one embodiment, the *Catharanthus* plant according to the present invention is an annual plant.

There is also provided a *Catharanthus* plant containing a genetic resistance to *Phytophthora*, obtainable by crossing with another *Catharanthus* plant wherein a sample of representative seed of a plant containing a genetic resistance to *Phytophthora* is deposited under NCIMB Accession No. 42348.

There is also provided a seed containing a genetic resistance to *Phytophthora*, wherein said seed is obtainable from a plant grown from seed deposited under NCIMB Accession No. 42348 or progeny thereof.

There is also provided a *Catharanthus* seed containing a genetic resistance to *Phytophthora*, wherein said seed has a pedigree which includes the plant FD0922, and wherein representative seed of said plant has been deposited under NCIMB Accession No. 42348.

There is also provided a *Catharanthus* seed containing a genetic resistance to *Phytophthora*, wherein said genetic resistance is present in FD0922, a representative sample of seed which is deposited at NCIMB under Accession No. NCIMB 42348, or in a progeny or ancestor thereof comprising said genetic resistance to *Phytophthora*.

In one embodiment, the genetic resistance to *Phytophthora* is not in the natural genetic background of the resistant *Catharanthus* plant. In one embodiment, the plant of the invention is an agronomically elite *Catharanthus* plant comprising a genetic resistance to *Phytophthora*.

In one embodiment, the *Catharanthus* seed contains an allele for resistance to the Syngenta (S) and Florida (F) isolates of *P. nicotianae*. The S and F isolates of *P. nicotianae* can be distinguished from one another using molecular techniques known to the person skilled in the art (Mammella et al, 2013). The F isolate is also known as Pn002-07 and was isolated from Orange County, Fla.

The resistance to the S strain is analogous to the originally what was patented in 1994 (see patent U.S. Pat. No. 5,491,285). All of the commercial hybrids are highly resistant to the S strain. No existing commercial hybrid is highly resistant to the F isolate.

In one embodiment, the plant according to the present invention displays high levels of resistance to *Phytophthora* infection, in particular the plant displays limited wilting or necrosis symptoms at the 14 DAI stage. The majority of the plants in the population are completely asymptomatic.

In one embodiment, the plant according to the present invention displays high levels of resistance to *Phytophthora* infection, in particular the plant displays limited wilting or necrosis symptoms at the 50 DAI.

In one embodiment, a plant according to the present invention belongs to the Cora series.

In one embodiment, a plant according to the present invention has resistance to *P. nicotianae* isolates with mating tape A1. In one embodiment, a plant according to the present invention has resistance to *P. nicotianae* isolates with mating type A2. In one embodiment, a plant according to the present invention has resistance to aerial *P. nicotianae*. There is also provided a *Catharanthus* plant produced by growing the seed of the present invention.

In one embodiment, the *Catharanthus* plant is a hybrid. In one embodiment, the *Catharanthus* plant is an inbred line.

There is also provided a tissue culture of cells produced from a *Catharanthus* plant of the present invention, wherein said cells of the tissue culture are produced from a plant part selected from the group consisting of seed, leaf, pollen, embryo, cotyledon, hypocotyl, meristematic cell, root, root tip, pistil, anther, flower, stem, and petiole.

There is also provided a *Catharanthus* plant regenerated from the tissue culture as herein described.

There is also provided pollen of the plant of the present invention.

There is also provided an ovule of the plant of the present invention.

There is also provided a method for producing $F_1$ hybrid *Catharanthus* seed comprising crossing a first parent *Catharanthus* plant with a second parent *Catharanthus* plant and harvesting the resultant $F_1$ hybrid *Catharanthus* seed, wherein said first or second parent *Catharanthus* plant is the *Catharanthus* plant of the present invention.

The present invention further relates to a method of producing the disclosed *Catharanthus* plant and seed by crossing a *Phytophthora* resistant plant of the instant invention with another *Catharanthus* plant. The invention also relates to the transfer of the genetic *Phytophthora* resistance into genera other than *Catharanthus*, including but not limited to the following genera: *Solanum, Capsicum, Eucalyptus, Carica, Ananas, Fragaria, Camellia, Castanea, Persea*, and citrus (Lamour, 2013).

In order to transfer the heritable genetic resistance to another plant, backcross breeding can be used. For this a desirable homozygous cultivar or inbred is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent (*Phytophthora* resistance, in particular to the Florida and Syngenta strains) are selected and repeatedly crossed (backcrossed) to the recurrent parent. The resulting plant is expected to have the attributes of the recurrent parent (e.g., cultivar) and the desirable trait transferred from the donor parent. Descriptions of other breeding methods that are commonly used for different traits and crops can be found in one of several reference books (Allard, 1960; Simmonds, 1979; Fehr, 1987).

A suitable donor parent for the genetic resistance to *Phytophthora* according to the present invention may be the *Catharanthus* plant FD0922, representative seeds of which have been deposited at NCIMB (Ferguson Building, Craibstone Estate, Bucksburn, Aberdeen AB219YA, Scotland) under NCIMB 42348 on Jan. 7, 2015.

Accordingly, the person skilled in the art, based on the description of the present invention and in possession of *Catharanthus* plant FD0922, representative seed of which is deposited under accession Number NCIMB 42348, has no difficulty transferring the genetic resistance to *Phytophthora* according to the present invention to any other *Catharanthus* plant using any breeding technique well known in the art.

There is also provided hybrid seed produced by the method of the present invention.

There is also provided a hybrid plant or its parts produced by growing hybrid seed of the present invention.

There is also provided seed containing a genetic factor to *Phytophthora* resistance produced from the hybrid plant of the present invention.

There is also provided viable *Catharanthus* seeds deposited under NCIMB Accession No. 42348 and plants grown from said deposited seeds and the progeny thereof, wherein the progeny contain the genetic factor for *Phytophthora* resistance.

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms “a”, “an”, and “the” include plural referents unless the context clearly dictates otherwise. Thus, for example, reference to “a plant” includes one or more plants.

As used herein, the term “breeding”, and grammatical variants thereof, refer to any process that generates a progeny individual. Breeding can be sexual or asexual, or any combination thereof. Exemplary non-limiting types of breeding include crossing, selfing, doubled haploid derivative generation, polyploidization and combinations thereof. The phenotype of the flower of the present invention can be readily and stably transferred by breeding to progeny.

As used herein, the term "hybrid" in the context of plant breeding refers to a plant that is the offspring of genetically dissimilar parents produced by crossing plants of different lines or breeds or species, including but not limited to the cross between two inbred lines.

A "cultivated *Catharanthus* plant" or an "elite *Catharanthus* plant" is understood within the scope of the invention to refer to a plant that is no longer in the natural state but has been developed by human care and for human use and/or consumption. "Cultivated plants" are further understood to exclude those wild-type species which comprise the trait being subject of this invention as a natural trait and/or part of their natural genetics.

A "plant" is any plant at any stage of development.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, callus, and the like.

As used herein, the term "population" means a genetically heterogeneous collection of plants sharing a common genetic derivation. A population of plants typically corresponds to 10 or more plants which have more or less the same phenotype at maturity in terms of flower color appearance.

As used herein, the term "progeny" refers to the descendant(s) of a particular cross. Typically, progeny result from breeding of two individuals, although some species (particularly some plants and hermaphroditic animals) can be selfed (i.e. the same plant acts as the donor of both male and female gametes). The descendant(s) can be, for example, of the $F_1$, the $F_2$, or any subsequent generation.

"Trait" is understood within the scope of the invention to refer to a characteristic or phenotype. A trait may be inherited in a dominant or recessive manner, or may be monogenic or polygenic.

"Dominant" is understood within the scope of the invention to refer to an allele which determines the phenotype when present in the heterozygous or homozygous state.

A "recessive" allele is only displayed when present in the homozygous state.

SEED DEPOSIT DETAILS

Seed of the variety FD0922 (a *Catharanthus roseus* plant) has been deposited under the terms of the Budapest Treaty on Jan. 7, 2015 at the NCIMB, Craibstone, Aberdeen, UK under number NCIMB 42348.

The seed deposit was made in the name of Syngenta Participations AG, Basel 4002, Switzerland.

EXAMPLES

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

Example 1

Resistance Breeding

The Cora series of *C. roseus* was introduced as resistant to *P. nicotianae*, but several instances of susceptibility to this pathogen were noted (Jeffers and Meadows, 2011). Consequently, three cultivars of *C. roseus*, two resistant (Cora Lavender, Cora Burgundy) and one susceptible (Titan Blush), were used to evaluate the virulence of 40 isolates of *P. nicotianae* that had been recovered from *C. roseus* over a 13-year period including four isolates from diseased Cora plants. All isolates also were tested for mating type and sensitivity to mefenoxam. Isolates varied significantly in virulence, cultivars varied significantly in susceptibility, and there was a significant isolate-by-cultivar interaction indicating that isolates affected cultivars differentially. Isolates were separated into three virulence groups: weakly, moderately, and highly virulent. Nine weakly virulent isolates caused little disease on any of the plants, and 21 moderately virulent isolates caused disease primarily on Titan Blush plants. The 10 highly virulent isolates caused disease on plants of all three cultivars often killing both Titan and Cora plants. Highly virulent isolates were mefenoxam sensitive and usually mating type A2.

Syngenta identified the *C. roseus* disease problem and decided to start a project of breeding resistance to aerial *Phytophthora*. Commercial *C. roseus* germplasm was used in early attempts to find resistance to aerial *Phytophthora*, but suitable resistance was not found from that source. Each accession was tested for aerial *Phytophthora* resistance, and one of them was found to be highly resistant. That acquisition served as the basis for all future resistance breeding to aerial *Phytophthora* in Syngenta.

*P. nicotianae* isolates used for resistance breeding came from a number of locations in California, Nevada, and Texas and all isolates showed similar levels of virulence when tested on *C. roseus* with the same level of resistance to aerial *Phytophthora*. At a point reasonably early in the resistance breeding program, one isolate out of 12 used for disease screening was chosen for future resistance breeding efforts. The chosen isolate came from an infected *C. roseus* plant grown in California.

The first seed *C. roseus* series resistant to *P. nicotianae* was the Cora *C. roseus* seed series in 2007 and was well accepted in the industry because Cora demonstrated strong resistance to *P. nicotianae* even when the weather conditions were very favorable to disease expression. There were, however, reports of susceptibility of Cora. The first report of Cora *C. roseus* being susceptible to aerial *Phytophthora* came from central Florida in 2007, with later reports coming from Georgia and south Florida.

In response to the reports of Cora's susceptibility, *C. roseus* resistance breeding within Syngenta was conducted using an isolate of *P. nicotianae* from south Florida that is virulent to Cora *C. roseus* named F isolate as well as another isolate of *P. nicotianae* that generates a similar disease response as the isolates that were used in the initial resistance breeding of Cora *C. roseus* named S isolate. This research identified a seed line (FD0922) highly resistant to both the S and F isolates of *P. nicotianae* by conducting a bioassay on the response to inoculation relative to that of known susceptible cultivars and existing Cora commercial hybrids. This patent application shows the high level of resistance of FD0922 to both the F and S isolates as a significant improvement over all known susceptible cultivars and existing Cora material.

Example 2

Ascertainment of Virulence Groups

The following cultivars were used in the study: Cultivar A (FD0922); Cultivar B (Cora Lavender); Cultivar C (Cora Cascade Cherry); and Cultivar D (Sunstorm Deep Pink—susceptible control).

The objective of the field trial was to determine if the four genotypes of annual *Vinca* were susceptible to isolates of *P. nicotianae* that are virulent to Cora plants.

There were 6 plants of each of 2 genotypes per container. This represented 12 plants/container and 18 plants/genotypexisolate combination Table 1 below shows the container number, together with the genotypes/replicate and corresponding treatments 1 to 5.

TABLE 1

| Cont # | Cultivar/Rep | Treatment |
|---|---|---|
| 1 | A1/C2 | 1 |
| 2 | B3/D2 | 4 |
| 3 | A1/D2 | 5 |
| 4 | B2/C1 | 4 |
| 5 | A3/B1 | 2 |
| 6 | B3/D2 | 1 |
| 7 | A1/B2 | 3 |
| 8 | A1/C3 | 2 |
| 9 | A2/D3 | 4 |
| 10 | C2/D1 | 5 |
| 11 | B1/C3 | 3 |
| 12 | C2/D1 | 2 |
| 13 | B1/C2 | 4 |
| 14 | A2/D3 | 2 |
| 15 | A3/B1 | 5 |
| 16 | A3/D1 | 4 |
| 17 | B2/C1 | 2 |
| 18 | C1/D3 | 3 |
| 19 | A3/D3 | 1 |
| 20 | C1/D3 | 5 |
| 21 | B3/D2 | 2 |
| 22 | A1/C3 | 4 |
| 23 | A2/B1 | 1 |
| 24 | D1/C3 | 1 |
| 25 | A2/C2 | 3 |
| 26 | A2/B3 | 5 |
| 27 | B2/C1 | 1 |
| 28 | B3/D2 | 3 |
| 29 | A3/D1 | 3 |
| 30 | B2/C3 | 5 |

An established field plot was used to evaluate four genotypes of annual *Vinca* to five inoculum treatments—one non-inoculated control treatment and four treatments comprised of different isolates of *P. nicotianae* (Table 2). Plants were received on 22 Aug. 2014 and planted in the 335-liter tubs containing Fafard 3B soilless container mix. Three replicates of each genotype were planted in the tubs with six plants per replicate. Two cultivars were planted in each tub using a split plot design. Plants were watered daily by an overhead irrigation system and were fertilized as needed using MiracleGro soluble fertilizer. After plants become established, soil in each tub was infested with inoculum from one of the treatments. Inoculum was produced by growing individual isolates on sterile vermiculite moistened with 10% V8 Juice broth at 25° C. for 3 weeks. Inoculum of individual isolates (Table 2) were pooled and thoroughly mixed to produce a composite batch of inoculum for each treatment. Plants were inoculated on 3 Sep. 2014 by mixing 200 ml of composite inoculum with 2000 ml of fresh Fafard 3B container mix and then spreading this mixture over the surface of each tub. Infested container mix was worked by hand into the top layer of container mix in the tub, and then tubs were watered thoroughly to incorporate the inoculum and prevent it from desiccating.

After inoculation, each plant was evaluated weekly for symptom severity using the following rating scale:
0=0% of plant showing symptoms [wilting or necrosis]—i.e., no symptoms, healthy
1=1-10% of plant showing symptoms
2=11-50% of plant showing symptoms
3=51-90% of plant showing symptoms
4=91-99% of plant showing symptoms
5=100% of plant showing symptoms—i.e., dead Plants were evaluated for 50 days after inoculation (about 7 weeks). Diseased plants were removed from the tubs and taken to in the laboratory for isolation. Stem and foliage tissues from representative plants of each genotype were placed on PARPH-V8 selective medium to confirm infection by *P. nicotianae*. Plates were held in the dark at 25° C. for 3-7 days to allow the pathogen to grow out from infected tissues. Data were analyzed by 2-way ANOVA using JMP Pro statistical software. Symptom severity scores were converted to the median value of the range before analysis:
0=0%
1=5.5%
2=30.5%
3=70.5%
4=95%
5=100%

In all, 19 isolates were used in this study, and all had been recovered from disease annual vinca plants between 1996 and 2008. All isolates were sensitive to the fungicide Subdue MAXX (a.i. mefenoxam), and both mating types were represented: 6 isolates were A1 and 13 isolates were A2. Isolates were divided into four groups based on virulence to 'Cora' vinca plants in a previous trial we conducted.

Treatment 1 was composed of 2 virulent isolates recovered from plants in South Carolina (SC) in 2002—before 'Cora' and 'Nirvana' plants had been released;

Treatment 2 was composed of 3 virulent isolates recovered from plants in SC in 2000, 2005, and 2008;

Treatment 3 was composed of virulent isolates recovered from 'Cora' or 'Nirvana' plants in Florida (FL) and Texas (TX) in 2007 and 2008; and Treatment 4 was composed of 10 avirulent isolates-8 recovered from plants in SC between 1996-2004 and 2 provided by Ball Horticultural Co. of unknown origin.

A summary of the treatments that were used in the field trial based on isolates of *Phytophthora nicotianae* recovered from diseased annual vinca plants are shown in Table 2.

TABLE 2

| Treatment no | Isolate no | Year isolated | Isolated by* | Mating type | Original location (City, State & Comments) |
|---|---|---|---|---|---|
| 1 | SC.02-1014 | 2002 | CU-PPC | A2 | Charleston, Sc. |
|   | SC.02-1263 | 2002 | CU-PPC | A2 | Seneca, SC |
| 2 | SC.00-1566 | 2000 | CU-PPC | A2 | Columbia, SC |
|   | SC.05-0162 | 2005 | CU-PPC | A2 | Columbia, SC |
|   | SC.08-0971 | 2008 | CU-PPC | A1 | Liberty, SC |
| 3 | PBF-1 | 2008 | SN Jeffers | A2 | Miami, FL |

TABLE 2-continued

| Treatment no | Isolate no | Year isolated | Isolated by* | Mating type | Original location (City, State & Comments) |
|---|---|---|---|---|---|
| | LB-845 | 2007 | Barnes-TAM | A2 | Orlando, FL |
| | LB-1134 | 2008 | Barnes-TAM | A2 | Miami, FL |
| | LB-1146 | 2008 | Barnes-TAM | A1 | San Antonio, TX |
| 4 | B69A-07 | Unknown | Ball Hort. | A2 | unknown |
| | B319-05 | Unknown | Ball Hort. | A2 | unknown |
| | SC.96-1553 | 1996 | CU-PPC | A2 | Anderson, SC |
| | SC.97-3179 | 1997 | CU-PPC | A1 | Mullins, SC |
| | SC.98-1442 | 1998 | CU-PPC | A2 | Cheraw, SC |
| | SC.00-1164 | 2000 | CU-PPC | A1 | Blackstock, SC |
| | SC.00-1223 | 2000 | CU-PPC | A1 | Columbia, SC |
| | SC.00-1975 | 2000 | CU-PPC | A2 | McCormick, SC |
| | SC.01-1700 | 2001 | CU-PPC | A1 | West Columbia, SC |
| | SC.04-1100 | 2004 | CU-PPC | A2 | Abbeville, SC |
| 5 | none = non-treated control | | | | |

*CU-PPC: from samples submitted to the Clemson University Plant Problem Clinic
SN Jeffers: samples submitted to the Jeffers lab at Clemson University
Barnes-TAM: Dr. Larry Barnes at Texas A & M University, College Station, TX P. nicotianae was isolated from all dead plants, so no other pathogens caused the death of the plants.

Three disease parameters were analyzed:
symptom severity at 50 DAI (the end of the trial)—see Tables 3-5 and FIG. 4;
survival time in number of days until a symptom severity score of 5 was reached—up to 50 DAI;
area under the disease progress curve (AUDPC)—which is the most meaningful parameter because it accounts for both virulence and aggressiveness of the isolates in the different treatments.

Many plants in Cultivar B (Cora Lavender) were alive at 50 DAI but had a symptom severity score of 3 or 4, so survival time is not the most meaningful disease parameter for cultivar evaluation.

For all three disease parameters, the treatment*cultivar interaction was highly significant (see Tables 3, 6, 9); however, this interaction is not the result of cultivars responding differentially by switching rank order. Instead, it was caused by a lack of disease in Treatment 5 (non-treated control) and only limited disease with Treatment 4 (avirulent isolates)—see FIGS. 4, 5, 6. Therefore, the main effects of cultivars over all five treatments were assessed, and the main effects of treatments over all four cultivars also were assessed.

Example 3

Symptom Severity

The symptom severity at 50 DAI (50 days after infection) are shown in Tables 3 to 5: All four cultivars differed in disease severity with Cultivar A (FD0922) being least susceptible by far with plants showing only 18.2% of tissue with symptoms, and Cultivar D (Sunstorm Deep Pink) most susceptible (plants were 79.8% symptomatic). Treatments 3, 2, and 1 were most virulent.

Table 3 is a 2-way ANOVA of symptom severity (%) at 50 days after inoculation. The effects of five inoculum treatments on four cultivars of annual vinca are shown

TABLE 3

| Source | df | F ratio | Prob > F |
|---|---|---|---|
| Inoculum treatments | 4 | 421.7 | <0.0001 |
| Cultivars | 3 | 490.1 | <0.0001 |

TABLE 3-continued

| Source | df | F ratio | Prob > F |
|---|---|---|---|
| 1Treatment *Cultivar interaction | 12 | 71.9 | <0.0001 |

Table 4 shows the differences among CULTIVARS with means separated by Fisher's protected least significant difference with P=0.05

TABLE 4

| Cultivar | Mean | Mean separation |
|---|---|---|
| D (Sunstorm Deep Pink) | 79.8 | A |
| C (Cora Cascade Cherry) | 60.8 | B |
| B (Cora Lavender) | 48.7 | C |
| A (FD0922) | 18.2 | D |

Table 5 shows the differences among TREATMENTS with means separated by Fisher's protected least significant difference with P=0.05.

TABLE 5

| Treatment | Mean | Mean separation |
|---|---|---|
| 3 | 80.4 | A |
| 2 | 76.9 | AB |
| 1 | 74.6 | B |
| 4 | 27.4 | C |
| 5 | <0.0001 | D |

Example 4

Survival Time

Tables 6 to 8 show how cultivars differed in susceptibility based on survival time. Cultivars A (FD0922) and B (Cora Lavender) survived longer than Cultivar C (Cora Cascade Cherry), and these three cultivars survived longer than Cultivar D (Sunstorm Deep Pink). All of the plants in Cultivar A (FD0922) survived the 50 days of this trial and most had only limited symptom development. Most of the plants in Cultivar B (Cora Lavender) also survived, but many of these had severe symptom development. Cultivars C (Cora Cascade Cherry) and D (Sunstorm Deep Pink) had a number of plants that died during the trial. Based on this parameter, Treatment 3 was the most virulent and Treatments 1, 2, and 3 showing varying degrees of virulence.

Table 6 is a 2-way ANOVA of survival in no. of days after inoculation (up to 50 DAI). The effects of five inoculum treatments on four cultivars of annual vinca are shown.

TABLE 6

| Source | df | F ratio | Prob > F |
|---|---|---|---|
| Inoculum treatments | 4 | 50.2 | <0.0001 |
| Cultivars | 3 | 281.1 | <0.0001 |
| Treatment *Cultivar interaction | 12 | 34.3 | <0.0001 |

Table 7 shows the differences among CULTIVARS with means separated by Fisher's protected least significant difference with P=0.05.

TABLE 7

| Cultivar | Mean | Mean separation |
|---|---|---|
| A (FD0922) | 50.0 | A |
| B (Cora Lavender) | 48.8 | A |
| C (Cora Cascade Cherry) | 37.0 | B |
| D (Sunstorm Deep Pink) | 30.8 | C |

Table 8 shows the differences among TREATMENTS with means separated by Fisher's protected least significant difference with P=0.05.

TABLE 8

| Treatment | Mean | Mean separation |
|---|---|---|
| 5 | 50.0 | A |
| 4 | 43.6 | B |
| 2 | 41.9 | BC |
| 1 | 39.9 | C |
| 3 | 33.1 | D |

Example 5

Area Under the Disease Progress Curve (AUDPC)

AUDPC is the most meaningful disease parameter because it takes into account disease development over the entire trial period of 50 DAI. As with symptom severity, all four cultivars differed in susceptibility with Cultivar A (FD0922) least susceptible and Cultivar D (Sunstorm Deep Pink) most susceptible. Treatment 3 was most virulent and Treatments 2 and 1 were more virulent than Treatment 4.

TABLE 9

| 2-way ANOVA | | | |
|---|---|---|---|
| Source | df | F ratio | Prob > F |
| Inoculum treatments | 4 | 565.5 | <0.0001 |
| Cultivars | 3 | 856.8 | <0.0001 |
| Treatment *Cultivar interaction | 12 | 93.5 | <0.0001 |

Table 10 shows the differences among CULTIVARS with means separated by Fisher's protected least significant difference with P=0.05

TABLE 10

| Cultivar | Mean | Mean separation |
|---|---|---|
| D (Sunstorm Deep Pink) | 3476 | A |
| C (Cora Cascade Cherry) | 2776 | B |
| B (Cora Lavender) | 1485 | C |
| A (FD0922) | 508 | D |

Table 11 shows the differences among TREATMENTS with means separated by Fisher's protected least significant difference with P=0.05.

TABLE 11

| Treatment | Mean | Mean separation |
|---|---|---|
| 3 | 3342 | A |
| 2 | 2957 | B |
| 1 | 2902 | B |
| 4 | 1105 | C |
| 5 | <0.0001 | D |

Example 6

Study Conclusions

Some plants in all cultivars developed foliage blight over the course of the 50 days of this trial, but relative susceptibility varied greatly among cultivars. Cultivar A (FD0922) was least susceptible and developed only minor symptoms. Alternatively, Cultivar D (Sunstorm Deep Pink) was most susceptible and many plants died before the trial was over. Overall, Treatment 3 was the most virulent, but Treatment 1 and 2 also showed a high degree of virulence. As expected, Treatment 4 was least virulent. These data indicate that Cultivar A (FD0922) has a high level of resistance to the virulent isolates of P. nicotianae that previously killed 'Cora' plants.

Example 7

Plant Material

The severity of disease of nine cultivars/lines was evaluated in response to S and F isolates of P. nicotianae. Four known fully susceptible cultivars were identified as controls and included Sunstorm Deep Pink, Sunstorm Apricot, Titan White, and Pacifica Icy Pink. Four existing Cora commercials were identified to depict differences in resistance to the S and F isolates and included Cora White, Cora Lavender, Cora Pink, and Cora Punch. One line was identified to depict high levels of resistance to both the S and F isolates of *P. nicotianae* and includes FD0922.

Two replicates/isolate type/sowing date were sown into 288-cell trays in Sunshine LP5 LL media under greenhouse conditions in Gilroy, Calif. over three dates, Nov. 7 2012 (S isolate avg. 23° C.), Jun. 11 2014 (S and F isolates avg. 25° C.), and Sep. 10 2014 (F isolate avg. 22° C.). Each replicate included 48 seedlings of each cultivar/line. Three weeks after sowing seedlings were saturated with $H_2O$ 1 hour prior to inoculation and inoculated with 1 mL of the *P. nicotianae* zoospore suspension applied directly to the soil. The soil was kept moist until completion of data collection.

Example 8

Disease Severity Data

Disease severity data was collected for each of the germinated seedlings (48 sown/cultivar) within each cultivar/line 14 days after inoculation. Data was collected Dec. 12 2012 (S isolate), Jul. 25 2014 (S and F isolates), and Oct. 16 2014 (F isolate).

The following rating scale as described by Jeffers (pers. comm.) was applied for each seedling:

TABLE 12

| Disease severity score | Description |
|---|---|
| 0 | Healthy, 0% of plant with symptoms (wilt, lesions, necrosis) |
| 1 | 1-10% of plant with symptoms (wilt, lesions, necrosis) |
| 2 | 11-50% of plant with symptoms (wilt, lesions, necrosis) |
| 3 | 51-90% of plant with symptoms (wilt, lesions, necrosis) |
| 4 | 91-99% of plant with symptoms (wilt, lesions, necrosis) |
| 5 | Dead, 100% of plant with symptoms (wilt, lesions, necrosis) |

Individual plant data was averaged for each cultivar/line, replicate, and sowing date and standard deviation was calculated (see Table 13; FIGS. 1 and 2). The temperature under which the plants were grown is shown in FIG. 3.

TABLE 13

Disease severity score averages of *Catharanthus roseus* cultivars/lines in response to S isolate and F isolates of *Phytophthora nicotianae* collected 14 days after inoculation. The disease severity scores were based on a scale of 0 to 5 where 0 = Healthy, 0% of plant with symptoms, 1 = 1-10% of plant with symptoms, 2 = 11-50% of plant with symptoms, 3 = 51-90% of plant with symptoms, 4 = 91-99% of plant with symptoms, and 5 = dead with 100% of plant with symptoms.

| C. roseus Cultivar/line | Company | Disease severity S Isolate | | Disease severity F Isolate | |
|---|---|---|---|---|---|
| | | December 2012 | July 2014 | July 2014 | October 2014 |
| Sunstorm Deep Pink | Syngenta | 5 | 5 | 5 | 5 |
| Titan White | PanAmerican | 5 | 5 | 5 | 5 |
| Pacifica Icy Pink | PanAmerican | 5 | 5 | 5 | 5 |
| Sunstorm Apricot | Syngenta | 5 | 5 | 4.99 ± 0.05 | 4.94 ± 0.28 |
| Cora Lavender | Syngenta | 0.047 ± 0.22 | 0.035 ± 0.16 | 3.16 ± 0.92 | 4.61 ± 0.48 |
| Cora Pink | Syngenta | 0 | 0.047 ± 0.15 | 3.84 ± 1.03 | 4.45 ± 0.58 |
| Cora Punch | Syngenta | 0.023 ± 0.11 | 0.023 ± 0.11 | 3.41 ± 1.01 | 3.48 ± 0.88 |
| Cora White | Syngenta | 0.034 ± 0.16 | 0.047 ± 0.17 | 4.48 ± 0.46 | 4.99 ± 0.052 |
| FD0922 | Syngenta | 0 | 0 | 0.044 ± 0.10 | 0.089 ± 0.18 |

The *Phytophthora nicotianae* inoculum was prepared as follows. *Catharanthus roseus* (*C. roseus*) seedlings were inoculated using a zoospore suspension applied directly to the soil. The production of *P. nicotianae* zoospores involves the following steps as outlined in Sandlin, 1993:

1) Preparation of V8 Juice Medium a. V8 juice agar medium was prepared by autoclaving a mixture of 200 mL V8 juice, 3 g $CaCO_3$, 15 g agar, and 800 mL $H_2O$ for 22 minutes at 121° C. The medium was then cooled and dispensed into sterile 100-x-10 mm petri plates.

2) Mycelial cultures were grown at room temperature on the V8 medium for 7 to 10 days prior to inoculation.

3) Soil extract was prepared in suspended garden soil (10 g/L) in DI $H_2O$.

4) Mycelial agar cultures were cut into 1.5 cm squares and rinsed in RO $H_2O$.

5) Agar squares were incubated in petri plates at 24° C. with 12 h light for 1 to 2 days to induce formation of sporangia.

6) To induce the formation and release of zoospores the soil extract of the petri plates was removed and replaced and submerged with fresh soil extract. The plates were then placed in a refrigerator (5° C.) for 30 min. Then the plates were removed and placed in room temperature for 1 hour for zoospore formation and release.

7) Zoospore inoculum was diluted to $1 \times 10^5$ zoospores/mL and applied to the soil.

LITERATURE CITED

Dastur, J. F. 1916. *Phytophthora* on *Vinca rosea*. Mem. Dep. Agric. India Bot. Ser. 8:233-242.

Gill, H. S., O. K. Ribeiro, and G. A. Zentmyer. 1977. *Phytophthora* blight of periwinkles in the Coachella Valley of California. Plant Dis. Rep. 61:560-561

Jeffers, S. N. and I. M. Meadows. 2011. Variation in virulence among isolates of *Phytophthora nicotianae* recovered from *Catharanthus roseus*. (Abstr.) Phytopathology 101 (Suppl.):S266.

Lamour, K. 2013. *Phytophthora*: a global perspective. CABI plant protection series (2).

Mammella, M. A., F. N. Martin, S. O. Cacciola, M. D. Coffey, R. Faedda, and L. Schena. 2013. Analyses of the population structure in a global collection of *Phytophthora nicotianae* isolates inferred from mitochondrial and nuclear DNA sequences. Phytopathology 103:610-622.

Keim, R. 1977. Foliage blight of periwinkle in Southern California. Plant Dis. Rep. 61:182-184

Fehr, W. R. 1987. Breeding methods for cultivar development. 293. In J. R. Wilcox (ed.) Soybeans: Improvement, and Uses. 2nd ed. Agronomy Monogr. 16. ASA, Madison, Wis.

Allard, R.1960 Principles of Plant Breeding. Wiley, New York, N.Y., 1st Ed.

Simmonds, N. W. 1979. Principles of crop improvement. Longman Group Ltd., London Sandlin, C. M. 1993. Effects of methyl bromide-chloropicrin fumigation of potting mix and length of irrigation period on severity and progression of root rot of Italian stone pine caused by *Phytophthora parasitica*. Doctoral dissertation, University of California, Riverside

The invention claimed is:

1. A *Catharanthus roseus* plant containing a genetic resistance to *Phytophthora nicotianae*, obtained by crossing a first *Catharanthus roseus* plant containing a genetic resistance to *Phytophthora nicotianae* with a second *Catharanthus roseus* plant, wherein a sample of representative seed of said *Catharanthus roseus* plant containing a genetic resistance to *Phytophthora nicotianae* is deposited under NCIMB Accession No: 42348.

2. The *Catharanthus roseus* plant of claim 1, wherein said seed contains a genetic resistance to the Syngenta (S) and Florida (F) isolates of *P. nicotianae*.

3. Pollen of the plant of claim 1.

4. An ovule of the plant of claim 1.

5. A method for producing $F_1$ hybrid *Catharanthus roseus* seed comprising crossing a first parent *Catharanthus roseus* plant with a second parent *Catharanthus roseus* plant and harvesting the resultant $F_1$ hybrid *Catharanthus roseus* seed, wherein said first or second parent *Catharanthus roseus* plant is the *Catharanthus roseus* plant of claim 1.

6. Viable *Catharanthus roseus* seed deposited under NCIMB Accession No: 42348, a plant grown from said deposited seed or a progeny thereof comprising the same genetic material for resistance to *Phytophthora nicotianae* as the seed deposited under NCIMB Accession No: 42348.

* * * * *